(12) United States Patent
Lee et al.

(10) Patent No.: US 9,931,443 B1
(45) Date of Patent: Apr. 3, 2018

(54) HEMOSTATIC INJECTION NEEDLE COATED WITH CROSSLINKED CHITOSAN HAVING CATECHOL GROUP AND OXIDIZED CATECHOL GROUP

(71) Applicant: INNOTHERAPY INC., Seoul (KR)

(72) Inventors: Haeshin Lee, Daejeon (KR); Mikyung Shin, Seoul (KR); Moon Sue Lee, Seoul (KR); Suk Song Oh, Chungcheongbuk-do (KR)

(73) Assignee: INNOTHERAPY INC., Seoul (KR)

( * ) Notice: Subject to any disclaimer, the term of this patent is extended or adjusted under 35 U.S.C. 154(b) by 0 days.

(21) Appl. No.: 15/559,414

(22) PCT Filed: Apr. 4, 2016

(86) PCT No.: PCT/KR2016/003451
§ 371 (c)(1),
(2) Date: Sep. 18, 2017

(87) PCT Pub. No.: WO2016/159734
PCT Pub. Date: Oct. 6, 2016

(30) Foreign Application Priority Data

Apr. 3, 2015 (KR) .......................... 10-2015-0047329

(51) Int. Cl.
*A61L 31/10* (2006.01)
*A61L 31/14* (2006.01)
*A61L 31/16* (2006.01)

(52) U.S. Cl.
CPC ............. *A61L 31/10* (2013.01); *A61L 31/145* (2013.01); *A61L 31/16* (2013.01); *A61L 2300/236* (2013.01); *A61L 2400/04* (2013.01); *A61L 2420/02* (2013.01)

(58) Field of Classification Search
CPC ........ A61L 31/10; A61L 31/145; A61L 31/16; A61L 2400/04; A61L 2300/236; A61L 2420/02

See application file for complete search history.

(56) References Cited

U.S. PATENT DOCUMENTS

2011/0311608 A1   12/2011   Roorda et al.

FOREIGN PATENT DOCUMENTS

| KR | 10-2012-0049419 A | 5/2012 |
| KR | 10-2013-0011354 A | 1/2013 |
| KR | 10-2013-0033996 A | 4/2013 |
| KR | 10-2013-0055847 A | 5/2013 |
| KR | 10-1576503 B1 | 12/2015 |
| WO | 2013077475 A1 | 5/2013 |

*Primary Examiner* — Trevor Love
(74) *Attorney, Agent, or Firm* — Hultquist, PLLC; Steven J. Hultquist (57) ABSTRACT

The present invention relates to a hemostatic injection needle coated with a chitosan in which a catechol group and an oxidized catechol group are introduced and cross-linked. The hemostatic injection needle according to the present invention can suppress bleeding during and after injection, and thus can be effectively used for injection not only into coagulopathy patients, including diabetic patients, patients under anticancer treatment, and haemophilia patients, who have a low hemostatic ability, but also into patients showing blood rejection responses, and children.

10 Claims, 5 Drawing Sheets
(5 of 5 Drawing Sheet(s) Filed in Color)

HEMOSTATIC INJECTION NEEDLE COATED WITH CROSSLINKED CHITOSAN HAVING CATECHOL GROUP AND OXIDIZED CATECHOL GROUP

CROSS-REFERENCE TO RELATED APPLICATIONS

This application is a U.S. national phase under the provisions of 35 U.S.C. § 371 of International Patent Application No. PCT/KR2016/003451 filed Apr. 4, 2016, which in turn claims priority of Korean Patent Application No. 10-2015-0047329 filed Apr. 3, 2015. The disclosures of such international patent application and Korean priority patent application are hereby incorporated herein by reference in their respective entireties, for all purposes.

TECHNICAL FIELD

The present invention relates to a hemostatic injection needle coated with a chitosan in which a catechol group and an oxidized catechol group are introduced and cross-linked.

BACKGROUND ART

The development of conventional hemostatic and adhesive products has been focused on their use in surgical operations. Typical medical hemostatic agents and adhesives include cyanoacrylate-based adhesives approved by the FDA, and fibrin glue based on in vivo blood clotting protein. However, such hemostatic and adhesive products do not satisfy all of adhesive strength, long-lasting properties after application, low toxicity, in vivo immune responses, etc. Thus, in the development of hemostatic agents, the development of materials having biocompatibility while having excellent adhesion to tissue has become an important issue.

Meanwhile, chitosan is widely known as a biopolymer having an excellent hemostatic ability. However, chitosan has disadvantages in that it has significantly low solubility in neutral solutions and is soluble only in acidic solutions. Due to such disadvantages, the use of chitosan as a medical material is limited.

Accordingly, studies have been reported on introducing the important functional group catechol that contributes to mussel adhesion, thereby increasing the solubility of chitosan and the adhesion of chitosan to mucosa and tissue. For example, International Patent Publication No. WO2013-077475 discloses an adhesive hydrogel composition comprising: a catechol group-coupled chitosan; and a Pluronic having a thiol group coupled to the end thereof. More particularly, it discloses an adhesive composition, which is stable in vivo and in vitro, is temperature-sensitive, has an excellent hemostatic effect, and thus can be used as a bioadhesive agent, and also discloses an adhesive agent, an anti-adhesive agent and a surface adsorption-preventing agent for medical use, which comprise the adhesive composition. Furthermore, a hydrogel or film formed using the catechol group-coupled chitosan has an excellent function so that it can substitute for conventional hemostatic agents that are used in surgical operations.

However, the formulation as described above is a form developed in view of convenience of surgical operations, and has a problem in that it does not satisfy all of adhesive strength, long-lasting properties after application, low toxicity, in vivo immune responses, etc.

Accordingly, the present inventors have conducted studies to develop a hemostatic injection needle which is a new type of medical device that does not cause any bleeding, and as a result, have found that an injection needle coated with a chitosan, in which a catechol group and an oxidized catechol group are introduced and cross-linked according to the present invention, can effectively suppress bleeding during and after injection, thereby completing the present invention.

SUMMARY OF INVENTION

It is an object of the present invention to provide an injection needle coating hydrogel for preventing bleeding during and after injection.

Another object of the present invention is to provide a hemostatic injection needle comprising the above-described injection needle coating hydrogel coated on the surface thereof.

Still another object of the present invention is to provide a method for manufacturing the above-described hemostatic injection needle.

Yet another object of the present invention is to provide an injection method that does not cause any bleeding using the above-described hemostatic injection needle.

To accomplish the above objet, the present invention provides a hydrogel for coating an injection needle which prevents bleeding during injection, which comprises a chitosan to which a catechol group is introduced and at least a portion of the catechol group is oxidized and cross-linked.

The present invention also provides a hemostatic injection needle comprising the above-described injection needle coating hydrogel coated on the surface thereof.

The present invention also provides a method of preparing the above-described hemostatic injection needle, the method comprising the steps of:

(1) preparing a solution of a chitosan in which a catechol group and an at least partially oxidized catechol group are introduced and partially cross-linked; and

(2) coating the surface of an injection needle with the solution of step (1).

The present invention also provides an injection method that does not cause bleeding, the method comprising the steps of:

(1) preparing a solution of a chitosan in which a catechol group and an at least partially oxidized catechol group are introduced and partially cross-linked;

(2) preparing a hemostatic injection needle by coating the surface of an injection needle with the solution of the step (1); and (3) performing injection into a human being or an animal by use of the hemostatic injection needle prepared in the step (2).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4, in graph (A), shows the results of UV-Vis spectrometry of a chitosan-catechol solution (red) used for manufacture of a hemostatic injection needle. The blue spectrum corresponds to a chitosan-catechol solution used as a control in which partial oxidation and cross-linking of catechol were not induced.

FIG. 4, in graph (B), shows the results of hydrogen nuclear magnetic resonance analysis of a chitosan-catechol solution (red) used for manufacture of a hemostatic injection needle.

FIG. 4, in spectra (C), shows rheological properties observed by exposing films, each formed of a chitosan-catechol solution, to saline (upper: a chitosan-catechol solution in which partial oxidation and cross-linking of catechol were not induced; lower: a chitosan-catechol solution used in Examples 1 to 3).

FIG. 5, in panels (A) through (C), shows in vivo experimental results for a hemostatic injection needle manufactured in Example 1. Specifically, FIG. 5, in panel (A) shows a hemostatic effect evaluated using a mouse saphenous vein model; FIG. 5, in panel (B) is a graph showing the amount of bleeding observed using a mouse saphenous vein model; and FIG. 5, in panel (C) shows a hemostatic effect evaluated using a rabbit ear vein model.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

Hereinafter, the present invention will be described in detail.

The present invention provides a hydrogel for coating an injection needle which prevents bleeding during injection, which comprises a chitosan to which a catechol group is introduced and at least a portion of the catechol group is oxidized and cross-linked.

Herein, the —OH group of the catechol group in the hydrogel is partially oxidized to an =O group, and then cross-linked by a dehydration-condensation reaction with an —NH$_2$ group contained in the chitosan, and the degree of oxidation of the catechol group is preferably 1 to 20% (on a molar basis) of the catechol group contained in the hydrogel. If the degree of oxidation of the catechol group is less than 1% of the catechol group contained in the hydrogel, there will be a problem in that cross-linking with the —NH$_2$ group contained in the chitosan is not sufficiently induced, and if the degree of oxidation of the catechol group is more than 20% but not more than 80% of the catechol group contained in the hydrogel, coating of the needle will be possible, but there will be a problem in that the degree of curing of the coated film increases so that the film cannot exhibit a hemostatic effect. If the degree of oxidation of the catechol group is more than 80% of the catechol group contained in the hydrogel, there will be a problem in that the degree of curing by cross-linking increases, and thus properties that are undesirable for coating the needle are obtained.

The expression "cross-linking by a dehydration-condensation reaction" means that, as shown in the following reaction scheme 1, the oxo (=O) group of the oxidized catechol group reacts with an amine (—NH$_2$) group positioned in a suitable orientation in the chitosan, thereby forming a bond.

Reaction Scheme 1 wherein the compound represented by formula 1 indicates the amine (—NH$_2$) group of the chitosan introduced with the catechol group and the oxidized catechol group wherein the compound represented by formula 2 indicates the oxidized catechol group of the chitosan introduced with the catechol group and the oxidized catechol group wherein the compound represented by formula 3 indicates a compound by a dehydration-condensation reaction between the compound represented by formula 1 and the compound represented by formula 2; and wherein L is a single bond, $C_{1-8}$ straight or branched-chain alkylene, or —C(=O)—$R^1$—, wherein $R^1$ is a single bond or $C_{1-8}$ straight or branched-chain alkylene.

Specifically, a precursor of the chitosan introduced with the catechol group and the oxidized catechol group is a chitosan not introduced with the oxidized catechol group, and the specific chemical structure of the chitosan introduced with the catechol group, used in the Examples below, is as shown in the following formula 4:

wherein x:y:z is preferably 6:1:3.

The present invention also provides a hemostatic injection needle comprising the above-described injection needle coating hydrogel coated on the surface thereof. Herein, the thickness of the hydrogel coated on the hemostatic injection needle is preferably 2 to 30 μm. If the thickness is less than 2 Gm, there will be a problem in that the hydrogel is included in an amount insufficient for preventing bleeding from occurring during and after injection, and thus bleeding is not effectively prevented, and if the thickness is more than 30 Gm, there will be a problem in that the thickness of the hydrogel coated on the needle is thick, and thus the hydrogel does not enter a living body together with the injection needle during injection and pushed by the skin, indicating that bleeding is not effectively prevented.

The present invention also provides a method for manufacturing the above-described hemostatic injection needle, the method comprising the steps of:

(1) preparing a solution of a chitosan in which a catechol group and an at least partially oxidized catechol group are introduced and partially cross-linked; and

(2) coating the surface of an injection needle with the solution of step (1).

Hereinafter, the method for manufacturing the hemostatic injection needle will be described in detail on a stepwise basis.

In the method for manufacturing the hemostatic injection needle according to the present invention, step (1) is a step of preparing a solution of a chitosan in which a catechol group and an at least partially oxidized catechol group are introduced and partially cross-linked.

In this case, the solution may be obtained by dissolving in a solvent a chitosan introduced with a catechol group and storing the chitosan solution to induce partial oxidation and cross-linking of the catechol group. Herein, the temperature for storing the chitosan is preferably 0 to 20° C., more preferably 2 to 10° C., much more preferably 3 to 5° C., most preferably 4° C. In addition, the time for storing the chitosan is preferably 1 to 5 days, more preferably 2 to 4 days, most preferably 3 days. The chitosan introduced with the catechol group is preferably contained in an amount of 1 to 2 wt %, more preferably 1.3 to 1.7 wt %, most preferably 1.5 wt %, based on the total weight of the solution.

If the chitosan storage temperature and time and the content of the chitosan introduced with the catechol group are out of the above-specified ranges, there may occur a problem in that the physical properties of a film required to coat the hemostatic injection needle are not obtained.

In the method for manufacturing the hemostatic injection needle according to the present invention, step (2) is a step of coating the surface of an injection needle with the solution of step (1). Specifically, step (2) is a step of placing the solution on the injection needle, and then uniformly coating the surface of the injection needle while rotating the injection needle at a certain speed.

In this case, the coating thickness of the injection needle may be adjusted depending on the amount of the solution used, and thus injection needles having a variety of different diameters may be coated.

The present invention also provides an injection method that does not cause bleeding, the method comprising the steps of:

(1) preparing a solution of a chitosan in which a catechol group and an at least partially oxidized catechol group are introduced and partially cross-linked;

(2) preparing a hemostatic injection needle by coating the surface of an injection needle with the solution of step (1); and

(3) performing injection into a human being or an animal by use of the hemostatic injection needle prepared in step (2).

Hereinafter, the injection method that does not cause bleeding will be described in detail on a stepwise basis.

In the injection method that does not cause bleeding according to the present invention, step (1) is a step of preparing a solution of a chitosan in which a catechol group and an at least partially oxidized catechol group are introduced and partially cross-linked.

In this case, the solution may be obtained by dissolving in a solvent a chitosan introduced with a catechol group and storing the chitosan solution to induce partial oxidation and cross-linking of the catechol group. Herein, the temperature for storing the chitosan is preferably 0 to 20° C., more preferably 2 to 10° C., much more preferably 3 to 5° C., most preferably 4° C. In addition, the time for storing the chitosan is preferably 1 to 5 days, more preferably 2 to 4 days, most preferably 3 days. The chitosan introduced with the catechol group is preferably contained in an amount of 1 to 2 wt %, more preferably 1.3 to 1.7 wt %, most preferably 1.5 wt %, based on the total weight of the solution.

If the chitosan storage temperature and time and the content of the chitosan introduced with the catechol group are out of the above-specified ranges, there may occur a problem in that the physical properties of a film required to coat the hemostatic injection needle are not obtained.

In the injection method that does not cause bleeding according to the present invention, step (2) is a step of preparing a hemostatic injection needle by coating the surface of an injection needle with the solution of step (1). Specifically, step (2) is a step of placing the solution on the injection needle, and then uniformly coating the surface of the injection needle while rotating the injection needle at a certain speed.

In this case, the coating thickness of the injection needle may be adjusted depending on the amount of the solution used, and thus injection needles having a variety of different diameters may be coated.

In the injection method that does not cause bleeding according to the present invention, step (3) is a step of performing injection into a human being or an animal by use of the hemostatic injection needle prepared in step (2).

Herein, the injection method that does not cause bleeding is characterized in that a coating layer on the surface of the hemostatic injection needle is exposed to a water-soluble environment in vivo and undergoes phase transition to a hydrogel that seals a punctured site caused by injection to thereby prevent bleeding. To ensure a sufficient time for conversion to the hydrogel, the hemostatic injection needle is preferably maintained in an injected state during 10 to 30 seconds after injection. If the time during which the hemostatic injection needle is maintained in vivo is less than 10 seconds, there will be a problem in that a sufficient time for conversion to the hydrogel is not ensured, and thus bleeding is not effectively prevented, and if the time during which the hemostatic injection needle is maintained in vivo is more than 30 seconds, a sufficient time for conversion to the hydrogel can be ensured, but there will be a problem in that a bruise occurs due to skin irritation.

The following experiments were performed to evaluate the hemostatic ability of the hemostatic injection needle according to the present invention.

First, the hemostatic injection needle manufactured in Example 1 was observed with a scanning electron microscope. As a result of the observation, it was found that the shape of the hemostatic injection needle manufactured in Example 1 was retained, and the surface of the injection needle was uniformly coated. In addition, the components of the coating layer on the surface of the hemostatic injection needle manufactured in Example 1 were analyzed by energy dispersive X-ray spectrometry. As a result of the analysis, it was fond that in the surface of the uncoated injection needle, elements such as chromium, iron and the like, which are the materials of the injection needle, were detected, whereas, in the surface of the hemostatic injection needle manufactured in Example 1, carbon, nitrogen, oxygen and the like, which are major elements contained in the catechol-functionalized chitosan, were detected (see FIG. 1 in Experimental Example 1).

In addition, in order to analyze the thickness of the coating film on the surface of the hemostatic injection needle manufactured in each of Examples 1 to 3, the film was separated and the thickness thereof was measured by a scanning electron microscope. As a result of the measurement, it was fond that as the thickness of each hemostatic injection needle increased, the thickness of the chitosan-catechol film formed was decreased by surface tension on the hemostatic injection needle. Specifically, it was found that the thicknesses of the film coated on the surface of the hemostatic injection needle manufactured in Examples 1 to 3 were 25.2±2.8 Gm, 26.6±3.0 m, and 3.8±0.7 Gm, respectively (see FIG. 2 in Experimental Example 2).

Further, and Ex Vivo experiment was performed to evaluate the hemostatic ability of the hemostatic injection needle manufactured in Example 1. As a result of the experiment, it was found that in the conventional injection needle, saline leakage occurred, whereas, in the hemostatic injection needle manufactured in Example 3, the puncture in the subcutaneous tissue was sealed and saline leakage was prevented, due to conversion of the coating film on the injection needle to a hydrogel, which occurred after 15 to 20 seconds after puncture of the subcutaneous tissue (see FIG. 3 in Experimental Example 3).

Figure 4:
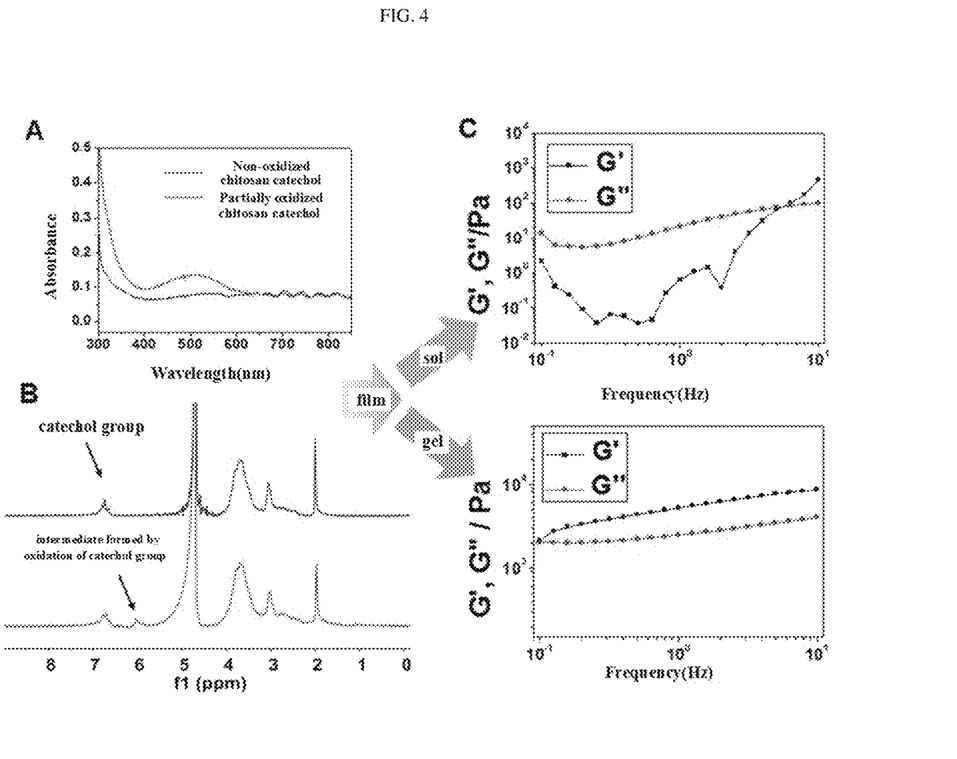

In addition, it was found that in order to verify conversion of the film on the surface of the hemostatic injection needle to the hydrogen as confirmed in Experimental Example 3, the properties of the chitosan-catechol solution used in the manufacture of the hemostatic injection needle were analyzed by UV-Vis spectrometry (see FIG. 4, in graph (A) in Experimental Example 4).

Further, in order to confirm the conversion of the coating film formed on the surface of the hemostatic injection needle to a hydrogel as can be seen in Experimental Example 3, analysis was performed by hydrogen[1] nuclear magnetic resonance spectrometry. As a result, it was found that an intermediate was formed by partial oxidation of catechol (see FIG. 4, in graph (B) in Experimental Example 4).

Besides, it was found that a film formed by drying 300 µL of the chitosan-catechol solution used in Examples was exposed to saline for 15 to 20 seconds, and then the formed material had the property of hydrogel (see FIG. 4, in spectra (C) in Experimental Example 4).

Figure 5:
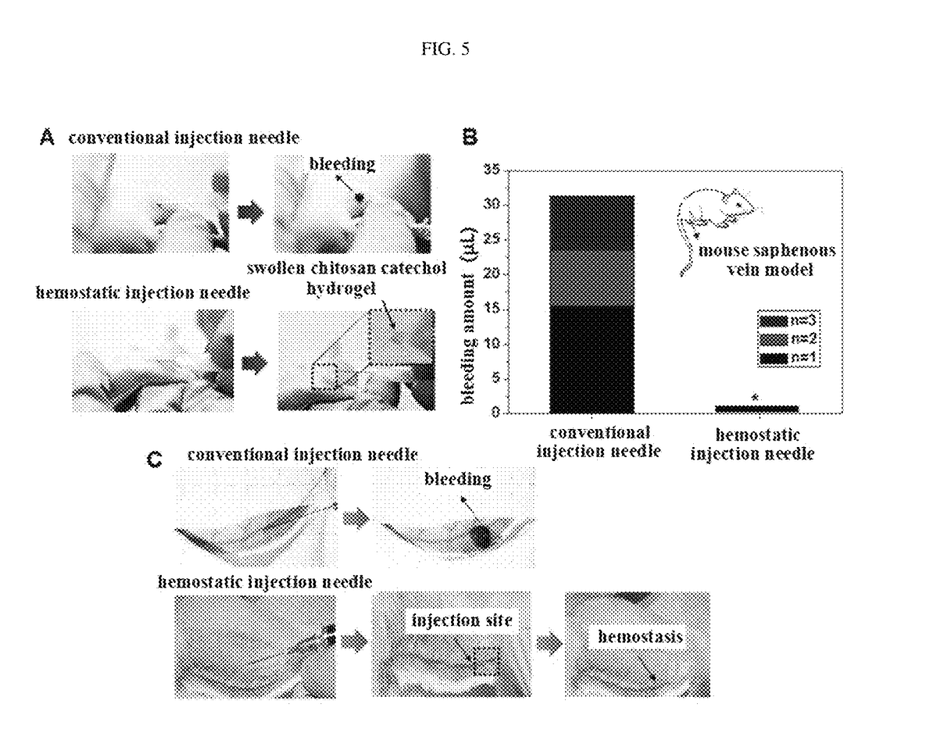

Further, an in vivo experiment was performed to evaluate the hemostatic ability of the hemostatic injection needle manufactured in Example 1. As a result of the experiment, it was found that in the hemostatic injection needle manufactured in Example 1, the coating formed from the chitosan-catechol solution was converted to a hydrogel and swollen, indicating that the hemostatic injection needle has a significantly better hemostatic effect compared to a conventional injection needle (see FIG. 5, in panel (A) in Experimental Example 5).

In addition, it was found that a conventional injection needle showed a total bleeding amount of 31.3 µL in a total of three experiments (n=3), whereas the hemostatic injection needle manufactured in Example 1 did not cause any bleeding (see FIG. 5, in panel (B) in Experimental Example 5). Further, it was found that the conventional injection needle caused bleeding during and after injection into the rabbit ear vein, whereas the hemostatic injection needle manufactured in Example 2 did not cause any bleeding during and after injection (see FIG. 5, in panel (C) in Experimental Example 5).

Therefore, the hemostatic injection needle according to the present invention can suppress bleeding during and after injection, and thus can be effectively used for injection not only into patients, including diabetic patients, patients under anticancer treatment, and haemophilia patients, who have a low hemostatic ability, but also into patients showing blood rejection responses, and children.

Hereinafter, the present invention will be described in further detail with reference to examples and experimental examples.

It will be obvious to a person having ordinary skill in the art that these examples and experimental examples are illustrative purposes only and are not to be construed to limit the scope of the present invention.

Preparation Example 1: Preparation of Chitosan Introduced with Catechol

3 g of about 30% acetylated chitosan (chitosan 70/100, model: 24204, manufactured by Heppe Medical Chitosan) was dissolved in 292 mL of HCl solution (pH=2) for 6 hours. The chitosan solution was adjusted to a pH of 5.5 by slowly adding 8 mL of 0.5 N NaOH solution thereto. The prepared 1% chitosan solution was stabilized for 12 hours.

To the prepared chitosan solution, 2.37 g of 3-(3,4-dihydroxyphenyl)propanoic acid was added. Then, as a reactant for forming an amide bond (—CONH—) between the amine (—NH$_2$) group of the chitosan and the carboxyl group (—COOH) of 3-(3,4-dihydroxyphenyl)propanoic acid, 2.02 g of 1-ethyl-3-(3-dimethylaminopropyl)carbodiimide (EDC) was dissolved in 50 mL of ethanol and added to the chitosan solution. Next, the solution was adjusted to a pH of 4.5, and then allowed to react for 1 hour. In this process, a catechol-functionalized chitosan was prepared.

To remove unreacted 3-(3,4-dihydroxyphenyl)propanoic acid and 1-ethyl-3-(3-dimethylaminopropyl)carbodiimide (EDC), the solution after the reaction was dialyzed in 4.5 L of triple-distilled water containing sodium chloride and 3 mL of 5 N HCl by use of a dialysis membrane (molecular weight cut-off: 12,000-15,000) for 3 days. Additionally, the solution was dialyzed in 4.5 L of triple-distilled water containing 3 mL of 5 N HCl for 2 days. Finally, the solution was dialyzed with triple-distilled water for 6 hours, and then freeze-dried, thereby preparing a catechol-functionalized chitosan (x:y:z=6:1:3).

Example 1: Manufacture 1 of Hemostatic Injection Needle (26 G)

1.5 mL of the catechol-functionalized chitosan prepared in Preparation Example 1 was dissolved in 100 μL of triple-distilled water, and then stored at 4° C. for 3 days to induce partial oxidation and cross-linking of the catechol group. As a result, a chitosan solution (hereinafter referred to as "chitosan-catechol solution" was prepared in which the catechol group OH)

and the oxidized catechol group were introduced and partially cross-linked.

The degree of oxidation of the catechol group in the chitosan-catechol solution was determined by measuring the absorbance at a wavelength of 500 nm by UV-Vis spectrometry. When a cross-link between the oxidized catechol group and the amine group of the chitosan is formed, the absorbance at a wavelength of 500 nm appears. Thus, based on the absorbance appearing the chitosan-catechol solution was treated with NaIO$_4$ (that is an oxidizing agent that induces oxidation of the chitosan-catechol solution to the highest possible degree) in an amount equal to three times the moles of the catechol group, the degree of oxidation of the chitosan-catechol solution was evaluated. As a result, it was shown that the degree of oxidation of the chitosan-catechol solution was 4.5 to 5.5%.

Meanwhile, for stable coating with the prepared chitosan-catechol solution, a 26 G-thick injection needle was treated with oxygen plasma for 10 minutes. Then, 6.5 μL of the chitosan-catechol solution was placed and coated on the injection needle at room temperature and a rotating speed of 40 rpm for 1 hour, and dried for 2 hours. This procedure was repeated twice, thereby manufacturing a hemostatic injection needle.

Example 2: Manufacture 1 of Hemostatic Injection Needle (23 G)

A hemostatic injection needle was manufactured in the same manner as described in Example 1, except that a 23 G-thick injection needle was used instead of the 26 G-thick injection needle and that the chitosan-catechol solution was used in an amount of 9 μL instead of 6.5 μL.

Example 3: Manufacture 3 of Hemostatic Injection Needle (18 G)

A hemostatic injection needle was manufactured in the same manner as described in Example 1, except that a 18 G-thick injection needle was used instead of the 26 G-thick injection needle and that the chitosan-catechol solution was used in an amount of 20 μL instead of 6.5 μL.

Experimental Example 1: Observation of Shape of Hemostatic Injection Needles The hemostatic injection needle manufactured in Example 1 was observed with a scanning electron microscope (Hitachi S-4800), and the results of the observation are shown in FIG. 1.

Figure 1:
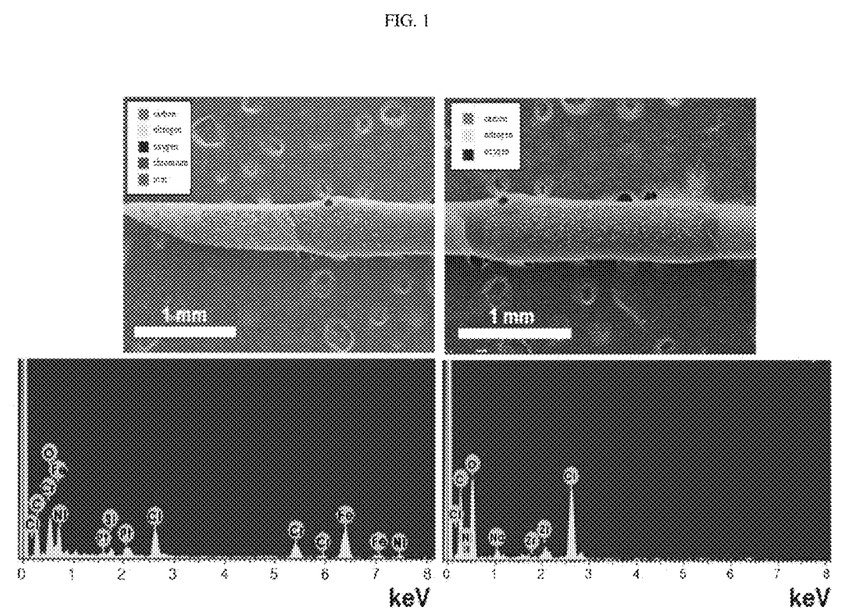
FIG. 1 depicts images the results of scanning electron microscopy performed to analyze the shape and components of a hemostatic injection needle manufactured in Example 1.

FIG. 1 depicts images the results of scanning electron microscopy performed to analyze the shape and components of a hemostatic injection needle manufactured in Example 1.

As shown in FIG. 1, the shape of the hemostatic injection needle manufactured in Example 1 was retained, and a chitosan-catechol solution was coated uniformly on the surface of the injection needle.

In addition, the components of the coating layer on the surface of the hemostatic injection needle manufactured in Example 1 were analyzed by energy dispersive X-ray spectrometry. Using an energy dispersive X-ray spectrometer attached to a scanning electron microscope, fluorescence X-rays occurring when measuring the coating layer on the surface the hemostatic injection needle manufactured in Example 1 were detected, and elements detected for 120 seconds were analyzed.

As a result, as shown in the graph at the bottom of FIG. 1, in the surface of the uncoated injection needle, elements such as chromium, iron and the like, which are the materials of the injection needle, were detected, whereas, in the surface of the hemostatic injection needle manufactured in Example 1, carbon, nitrogen, oxygen and the like, which are major elements contained in the catechol-functionalized chitosan, were detected.

Thus, it was shown that the hemostatic injection needle according to the present invention was exactly manufactured.

Experimental Example 2: Analysis of Thickness

To analyze the thickness of the coating film on the surface of the hemostatic injection needle manufactured in each of Examples 1 to 3, the film was separated and the thickness thereof was measured by a scanning electron microscope (Hitachi S-4800). The results of the measurement are shown in FIG. 2.

Figure 2:
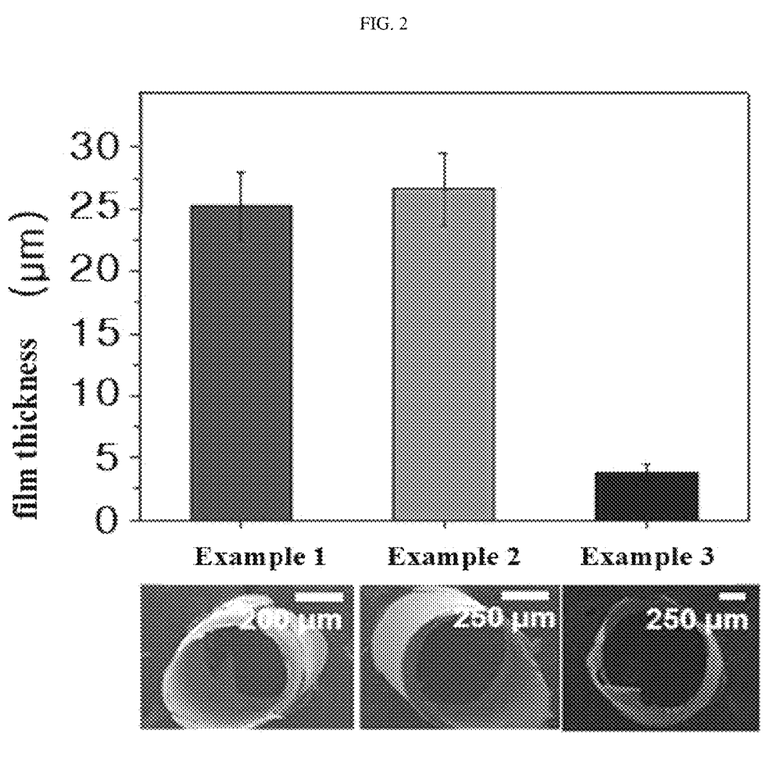
FIG. 2 is a graph showing the thickness of a film coated on each of hemostatic injection needles manufactured in Examples 1 to 3, and images at the bottom of FIG. 2 show film shapes measured by scanning electron microscopy.

FIG. 2 is a graph showing the thickness of a film coated on each of hemostatic injection needles manufactured in Examples 1 to 3, and images at the bottom of FIG. 2 show film shapes measured by scanning electron microscopy.

As shown in FIG. 2, as the thickness of each hemostatic injection needle increased, the thickness of the chitosan-catechol film formed was decreased by surface tension on the hemostatic injection needle. However, since the difference in thickness between the hemostatic injection needle of Example 1 (26 G) and the hemostatic injection needle of Example 2 (23 G) was not great, there was no great difference in the thickness of the film on the surface between Example 1 and Example 2. Specifically, the thicknesses of the film coated on the surface of the hemostatic injection needle manufactured in Examples 1 to 3 were 25.2±2.8 Gm, 26.6±3.0 m, and 3.8±0.7 Gm, respectively.

Experimental Example 3: Ex Vivo Evaluation of Hemostatic Ability

Figure 3:
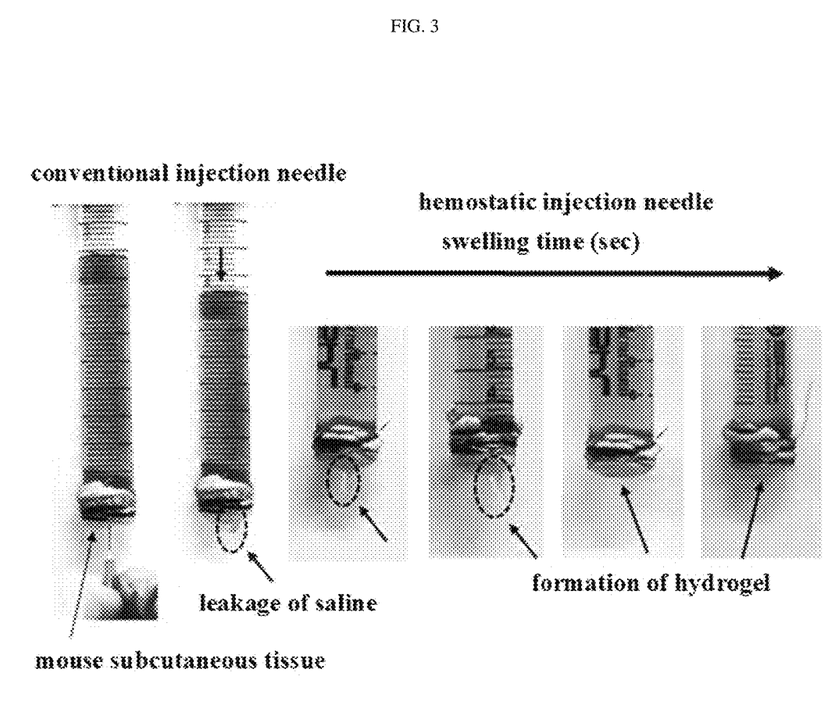
FIG. 3 shows ex vivo experiments performed to confirm the hemostatic mechanism of a hemostatic injection needle manufactured in Example 1.

To evaluate the hemostatic ability of the hemostatic injection needle manufactured in Example 3, an ex vivo experiment was performed as shown in FIG. 3. Specifically, one end of each syringe tube was blocked with the subcutaneous tissue of nude mice (BALBc nude mice, 8-week-old, male, 23 to 25 g), and each syringe tube was filled with saline. Then, the subcutaneous tissue was punctured with the hemostatic injection needle (18 G) manufactured in Example 3 or a conventional injection needle, and whether or not saline would leak through the puncture was observed.

FIG. 3 shows ex vivo experiments performed to confirm the hemostatic mechanism of a hemostatic injection needle manufactured in Example 1.

As shown in FIG. 3, in the conventional injection needle, saline leakage occurred, whereas, in the hemostatic injection needle manufactured in Example 3, the puncture in the subcutaneous tissue was sealed and saline leakage was prevented, due to conversion of the coating film on the injection needle to a hydrogel, which occurred after 15 to 20 seconds after puncture of the subcutaneous tissue.

Experimental Example 4: Analysis of Film Properties to Confirm Hemostatic Mechanism In order to verify conversion of the film on the surface of the hemostatic injection needle to the hydrogen as confirmed in Experimental Example 3, the properties of the chitosan-catechol solution used in the manufacture of the hemostatic injection needle were analyzed by UV-Vis spectrometry (HP8453, Hewlett Packard). The results of the analysis are shown in FIG. 4, in graph (A).

FIG. 4, in graph (A) shows the results of UV-Vis spectrometry of a chitosan-catechol solution (red) used for manufacture of a hemostatic injection needle. The blue spectrum corresponds to a chitosan-catechol solution used as a control in which partial oxidation and cross-linking of catechol were not induced.

As shown in FIG. 4, in graph (A), the measurement results of UV-Vis spectrometry showed absorbance at a wavelength of 500 nm, and thus catechol in the chitosan-catechol solution was partially oxidized.

Furthermore, analysis was performed by hydrogen[1] nuclear magnetic resonance spectrometry (Bruker AV-300). As a result, as shown in FIG. 4, in graph (B), an intermediate was formed by partial oxidation of catechol.

FIG. 4, in graph (B) shows the results of hydrogen[1] nuclear magnetic resonance analysis of a chitosan-catechol solution (red) used for manufacture of a hemostatic injection needle.

Furthermore, a film formed by drying 300 μL of the chitosan-catechol solution was exposed to saline for 15 to 20 seconds, and then the formed material was analyzed by a rheometer (Bohlin Advanced Rheometer, Malvern Instruments). As a result, as shown in FIG. 4, in spectra (C), the formed material had the property of hydrogel.

FIG. 4(C) is a graph showing rheological properties observed by exposing films, each formed of a chitosan-catechol solution, to saline (upper: a chitosan-catechol solution in which partial oxidation and cross-linking of catechol were not induced; lower: a chitosan-catechol solution used in Examples 1 to 3).

Specifically, a film formed from the chitosan-catechol solution used in Examples 1 to 3 was placed on the sample holder of a rheometer, the degree of deformation of the material was analyzed based on storage modulus (G') and loss modulus (G") while a shear stress of 100 Pa was applied at a frequency of 0.1-10 rad/sec by use of a 20 mm-thick parallel plate. Storage modulus (G') and loss modulus (G") were calculated using the following equation 1:

$$\sigma = \gamma_0 [G'(\omega)\sin(\omega t) + (G''(\omega)\cos(\omega t)]$$ Equation 1 wherein σ is a shear stress applied to the material;
$\gamma_0$ is a maximum amplitude of a shear strain appearing by the deformation of the material;
G' is a storage modulus;
G" is a loss modulus;
ω is a frequency; and
t is a time.

As shown in the upper portion of FIG. 4, in spectra (C), the film formed from the chitosan-catechol solution in which the oxidation and cross-linking of the catechol are not introduced partially showed the loss modulus (G") was greater than the storage modulus (G') in the most region, indicating that no hydrogel was formed.

However, as shown in the lower portion of FIG. 4, in spectra (C), the film formed from the chitosan-catechol solution used in Examples 1 to 3 showed storage modulus (G') greater than loss modulus (G") in the entire region, indicating that hydrogel was formed.

Experimental Example 5: In Vivo Evaluation of Hemostatic Ability

To evaluate the hemostatic abilities of the hemostatic injection needles manufactured in Examples 1 and 2, the following experiment was performed.

First, mouse saphenous vein models (BALBc nude mice, 8-week-old males, 23 to 25 g) and rabbit ear vein models (New Zealand white rabbits, 12-14-week-old females, 2.5 to 3.0 kg) were prepared. Next, to ensure a sufficient time during which the film coated on the surface of the hemostatic injection needle manufactured in Example 1 or 2 would be converted to a hydrogel, the injection needle was withdrawn at 20 seconds after injection. The results are shown in FIG. 5, in panels (A) through (C).

FIG. 5, in panels (A) through (C), shows in vivo experimental results for a hemostatic injection needle manufactured in Example 1 or 2. Specifically, FIG. 5, in panel (A) shows a hemostatic effect evaluated using a mouse saphenous vein model through an injection needle manufactured in Example 1; FIG. 5, in panel (B) is a graph showing the amount of bleeding observed using a mouse saphenous vein model; and FIG. 5, in panel (C) shows a hemostatic effect evaluated using a rabbit ear vein model through an injection needle manufactured in Example 2.

As shown in FIG. 5, in panel (A), in the hemostatic injection needle manufactured in Example 1, the coating formed from the chitosan-catechol solution was converted to a hydrogel and swollen, indicating that the hemostatic injection needle has a significantly better hemostatic effect compared to a conventional injection needle.

In addition, as shown in FIG. 5, in panel (B), a conventional injection needle showed a total bleeding amount of 31.3 μL in a total of three experiments (n=3), whereas the hemostatic injection needle manufactured in Example 1 did not cause any bleeding.

Furthermore, as shown in FIG. 5, in panel (C), the conventional injection needle caused bleeding during and after injection into the rabbit ear vein, whereas the hemostatic injection needle manufactured in Example 2 did not cause any bleeding during and after injection.

Therefore, the hemostatic injection needle coated with a solution of a chitosan in which a catechol group and an oxidized catechol group are introduced and partially cross-linked according to the present invention can suppress bleeding during and after injection, and thus can be effectively used for injection not only into patients, including diabetic patients, patients under anticancer treatment, and haemophilia patients, who have a low hemostatic ability, but also into patients showing blood rejection responses, and children.

INDUSTRIAL APPLICABILITY

The hemostatic injection needle according to the present invention can suppress bleeding during and after injection, and thus can be effectively used for injection not only into patients, including diabetic patients, patients under anticancer treatment, and haemophilia patients, who have a low hemostatic ability, but also into patients showing blood rejection responses, and children.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A hydrogel coating on a hemostatic injection needle which prevents bleeding during injection, said coating comprising a chitosan to which a catechol group is introduced and at least a portion of the catechol group is oxidized and cross-linked.

2. The hydrogel coating on a hemostatic injection needle of claim 1, wherein the —OH group of the catechol group in the hydrogel is partially oxidized to an =O group, and then cross-linked by a dehydration-condensation reaction with an —NH₂ group contained in the chitosan.

3. The hydrogel coating on a hemostatic injection needle of claim 1, wherein a degree of oxidation of the catechol group is 1 to 20% (on a molar basis) of the catechol group contained in the hydrogel.

4. A hemostatic injection needle comprising a hydrogel coating on a surface thereof, said hydrogel coating having a thickness in a range of from 2 to 30 μm, and comprising a chitosan to which a catechol group is introduced and at least a portion of the catechol group is oxidized and cross-linked.

5. The hemostatic injection needle of claim 1, wherein a thickness of the hydrogel coated on the hemostatic injection needle is 2 to 30 μm.

6. A method of preparing the hemostatic injection needle of claim 4, comprising:
   (1) Preparing a chitosan solution in which a catechol group and an at least partially oxidized catechol group are introduced and partially cross-linked; and
   (2) coating a surface of an injection needle with the solution of step (1).

7. The method of claim 6, wherein the step (2) comprises a step of placing the chitosan solution in which the catechol group and the oxidized catechol group are introduced and partially cross-linked on the injection needle, and then coating the surface of the injection needle while rotating the injection needle at a predetermined speed.

8. The method of claim 6, wherein a coating thickness of the injection needle is adjusted depending on an amount of the chitosan solution.

9. A hemostatic injection method comprising:
   (1) Preparing a chitosan solution in which a catechol group and an at least partially oxidized catechol group are introduced and partially cross-linked;
   (2) preparing a hemostatic injection needle by coating a surface of an injection needle with the solution of the step (1); and (3) performing injection into a human being or an animal by the hemostatic injection needle prepared in step (2).

10. The hemostatic injection method of claim 9, wherein a punctured site caused by injection is sealed and is prevented from bleeding by the hydrogel, which is formed in vivo when exposed to a water soluble environment, and which is coated on the surface of the hemostatic injection needle.

\* \* \* \* \*